(12) United States Patent
Lee et al.

(10) Patent No.: US 8,827,920 B2
(45) Date of Patent: Sep. 9, 2014

(54) TELEMEDICAL STETHOSCOPE

(75) Inventors: Byung Hoon Lee, Seoul (KR); Ju Han Kim, Seoul (KR)

(73) Assignees: Byung Hoon Lee, Seoul (KR); Seoul National University R&DB Foundation, Seoul (KR)

( * ) Notice: Subject to any disclaimer, the term of this patent is extended or adjusted under 35 U.S.C. 154(b) by 0 days.

(21) Appl. No.: 14/008,795

(22) PCT Filed: Aug. 19, 2011

(86) PCT No.: PCT/KR2011/006146
§ 371 (c)(1),
(2), (4) Date: Dec. 6, 2013

(87) PCT Pub. No.: WO2012/133998
PCT Pub. Date: Oct. 4, 2012

(65) Prior Publication Data
US 2014/0107515 A1    Apr. 17, 2014

(30) Foreign Application Priority Data

Mar. 30, 2011  (KR) .................. 10-2011-0028750

(51) Int. Cl.
| | | |
|---|---|---|
| *A61B 5/02* | (2006.01) | |
| *A61B 5/12* | (2006.01) | |
| *A61B 5/00* | (2006.01) | |
| *A61B 7/00* | (2006.01) | |
| *A61B 7/04* | (2006.01) | |
| *A61B 7/02* | (2006.01) | |

(52) U.S. Cl.
CPC . *A61B 7/04* (2013.01); *A61B 5/742* (2013.01); *A61B 7/008* (2013.01); *A61B 5/0004* (2013.01); *A61B 5/741* (2013.01); *A61B 7/003* (2013.01); *A61B 5/7282* (2013.01); *A61B 5/7225* (2013.01); *A61B 5/7203* (2013.01); *A61B 7/026* (2013.01)
USPC .......................................... 600/528; 600/523

(58) Field of Classification Search
USPC ................................. 600/523, 528
See application file for complete search history.

(56) References Cited

U.S. PATENT DOCUMENTS

| | | | |
|---|---|---|---|
| 2002/0188227 A1* | 12/2002 | Chong et al. ................. | 600/586 |
| 2004/0092846 A1* | 5/2004 | Watrous ........................ | 600/586 |
| 2005/0043643 A1* | 2/2005 | Priemer ........................ | 600/528 |

* cited by examiner

*Primary Examiner* — Christopher D Koharski
*Assistant Examiner* — Michael Carey
(74) *Attorney, Agent, or Firm* — Stein IP, LLC (57) ABSTRACT

The present invention relates to a telemedical stethoscope, which automatically diagnoses a disease, and records visually and auditorily, and stores the stethoscope data on a screen. The present invention enhances primary diagnosis and treatment effect for a patient by transmitting/receiving the data to/from a doctor at a medical center and by receiving a telemedicine service. In addition, the present invention transmits the data to a health management program so as to be used for personal healthcare and disease prognosis decision of a patient.

7 Claims, 10 Drawing Sheets

Heart (H) Main Auscultation Region

FIG. 4a

Heart (H) Cutting Region

Heart (H) Pulmonary (P) Main Auscultation Region

TELEMEDICAL STETHOSCOPE

CROSS-REFERENCE TO RELATED APPLICATIONS

This application is a national stage application of International Application No. PCT/KR2011/006146, filed Aug. 19, 2011, published as U.S. Patent Publication No. 2014/0107515 on Apr. 17, 2014, which claims the benefit of Korean Application No. 10-2011-0028750, filed Mar. 30, 2011, in the Korean Intellectual Property Office. All disclosures of the document(s) named above are incorporated herein by reference.

BACKGROUND OF THE INVENTION

1. Field of the Invention

The present invention relates to a telemedical stethoscope that determines a disease name and stores auscultation data. Also, the present invention causes a patient to transmit/receive auscultation data to/from a doctor in a medical center to receive a telemedicine service and transmits the auscultation data to a health management program to be helpfully used for a personal health management and a disease prognosis determination.

2. Description of the Related Art

Various electronic diagnosis devices are equipped in a modern general hospital and helps for a diagnostic workup.

However, when a doctor diagnoses a patient before the doctor uses such electronic diagnosis devices, the doctor carefully listens to a patient medical history to primarily diagnose a disease through an anthroposcopy, a manipulation, a percussion, an auscultation through a stethoscope or a hematomanometer.

Then, the doctor weighs a relative seriousness of a disease through a synthesized overhaul to definitely diagnose the disease and cure the disease.

Recently, the doctor prefers auscultation through an electronic stethoscope rather than that through a doctor's gut feeling in the primary diagnose for the patient.

The prior arts for an electronic stethoscope may include Japanese Utility model Registration No. 64-50805, for example. An electronic stethoscope includes a device recording a sound as a graph, a microphone detecting a sound and an earphone being worn in an ear. The electronic stethoscope electronically converts an auscultation sound to cause only a doctor to listen to the auscultation sound.

Also, an electronic stethoscope with a timing sound in U.S. Pat. No. 5,003,605 includes an electronic circuit that amplifies a frequency of an auscultation sound to display the auscultation sound as a visual graph.

Also, an electronic stethoscope with a hematocele indicator in U.S. Pat. No. 4,783,813 visually displays a hematocele and a respiratory sound for an expert doctor Also, an electronic stethoscope in U.S. Pat. No. 4,598,417 includes an electronic circuit that amplifies a frequency of an auscultation sound to the auscultation sound with an earphone for a medical check-up.

Also, an electronic stethoscope in U.S. Pat. No. 4,254,302 includes a microphone, an electronic amplification circuit and a power supply in a sound collecting plate to listen to an auscultation sound alone through a mini speaker and through a sound tube worn in both ears.

The electronic stethoscope disclosed in the above prior arts amplifies an auscultation sound to be heard alone and the auscultation sound may not be heard by many people.

The applicant developed an electronic stethoscope for hearing an auscultation sound by many people to register a Patent and Utility model.

For example, Korean Utility model Registration No. 0131518 (Dec. 15, 1998) and U.S. Pat. No. 5,737,429 discloses a portable watch-type stethoscope having a simple configuration without a rubber sound tube and earing and having an electronic amplification circuit, speaker and a display in inner of stethoscope case configured with two small and large sound collecting plates collecting a sound to amplify the auscultation sound to be audibly heard and to display a wave of an auscultation frequency as a graph in the display to be watched by many people.

Also, Korean Patent Registration No. 10-0387201 (Jun. 12, 2003) and U.S. Pat. No. 6,520,924 discloses an automatic determination storing diagnosis device that filters a noise external of a body from an auscultation sound detected in an auscultation microphone to convert the filtered analog wave data into digital data through an A/D converter, compares the digital data with standard auscultation sound data for various kinds of diseases to determine a disease name, stores the disease name in a storing device and displays the disease name through a plurality of monitors.

Also, U.S. patent application Ser. No. 11/885,108, which is a national stage application of International Application No. PCT/KR2005/003800, filed Nov. 10, 2005, published as U.S. Patent Publication No. 2008/0146276, on Jun. 19, 2008, and issued as U.S. Pat. No. 8,200,277, on Jun. 12, 2012, discloses a mobile phone with a stethoscope transmitting and receiving auscultation data auscultated thereby through transmitting and receiving function of the mobile phone to a remote location to receive a telemedicine service.

An automatic determination storing diagnosis device in Korean Patent Registration No. 10-0287201 and U.S. Pat. No. 6,520,924 related with the present invention has advantageous effects that automatically determines and stores a disease name from an auscultation sound and secures objectivity for the disease name.

Also, a portable watch-type stethoscope in Korean Utility model Registration No. 0131518 and U.S. Pat. No. 5,737,429 embeds a microphone in a sound collecting tube of a sound collecting plate to convert an auscultation sound in an inner body into an electrical signal and to cause a doctor to listen to and watch a body sound with a speaker and display.

Also, a mobile phone with a stethoscope in Korean Utility model Registration No. 0389343 and PCT Patent Application No. PCT/KR2005/003800 has advantageous effects that transmits and receives auscultation auscultated thereby through transceiver function in the mobile phone to a remote location to receive a telemedicine service.

However, a conventional stethoscope in the above does not designate an auscultation object, an auscultation region and an auscultation order and does not easily distinguish what object in a region of a body auscultation data received through a microphone of a sound collecting plate is. Also, because a conventional stethoscope filters only noise external of a body and the filtered data includes heart pulsation sound, a lung respiratory sound, a blood flow sound of a cervical carotid artery and a bowel movement sound, there is more comparison and more determination error in case where the conventional stethoscope compares standard data for various kinds of diseases with the filtered data and an accuracy of the determination is lower.

SUMMARY OF THE INVENTION

Therefore, for improving the above disadvantages, the present invention auscultates according to an auscultation region and an auscultation order in the auscultation mode designated by the designation switch (Hs) for the heart region auscultation mode (H), the designation switch (Ps) for the pulmonary region auscultation mode (P), the designation switch (Ns) for the neck carotid artery region auscultation mode (N) and the designation switch (Bs) for the bowel region auscultation mode (B), compares auscultation data detected in the auscultation mode with standard data in each designation mode to decode the auscultation data and automatically determine a disease name and stores the auscultation data. Then the present invention relates to a telemedical stethoscope that transmits and receives the auscultation data to/from a doctor and transmits the auscultation data to a telemedicine and health management application program to increase a health management effect.

An object of the present invention provides a telemedical stethoscope that may distinguish auscultation objects to set four auscultation modes and to cause inner units in the stethoscope to operate by a program of the auscultation mode, display an auscultation region and auscultation order in a display unit of the stethoscope when the auscultation mode is designated and auscultate according to the auscultation order to obtain auscultation data per the auscultation mode.

Another object of the present invention provides a telemedical stethoscope that may compare standard data with detected data by limiting a search scope to the standard data in a designated mode among all standard data in various kinds of diseases, automatically display a disease name and increase diagnosis correctness.

Still another object of the present invention provides a telemedical stethoscope that may audiovisually record and store a result diagnosed per the auscultation mode and remotely transmit to provide a telemedicine server to a patient.

Still another object of the present invention provides a telemedical stethoscope that may transmit diagnosis data to a an attached device linked a health management program and use for a disease prognosis and personal health management.

A telemedical stethoscope of the present invention includes a central control device and a power supply built in inner of a case which is integrally equipped with a sound collecting plate embedding an auscultation microphone through a support pipe. An LCD (Liquid Crystal Display) is linearly built on the case and a switch block including a power switch, a watch switch and a remote transceiver switch is built on one side of the case. A mode switch block, a speaker for data auralization and an antenna for remote data transceiver is built on another side of the case. The mode switch block includes a designation switch for a heart region auscultation mode, a designation switch for a pulmonary region auscultation mode, a designation switch for a neck carotid artery region auscultation mode and a designation switch for a bowel region auscultation mode.

The central control device in the telemedical stethoscope includes an auscultation unit configured to designate an auscultation mode, a detection unit for the auscultation microphone, a filter unit configured to filter an auscultation sound of the designated auscultation mode in a detected auscultation sound to remove other auscultation sound in the detected auscultation, an auscultation amplification unit configured to amplify the filtered auscultation sound, an ADC configured to convert an analog signal of the amplified auscultation sound into a digital signal, a digital signal amplification unit to amplify the converted digital signal, a database storing standard data for various kinds of diseases per the auscultation mode, a comparing unit configured to compare the amplified digital signal with the standard data in the auscultation mode, a central control unit configured to determine a disease name based on the compared result and to control each unit, a storage unit configured to store the determined disease name, a display unit configured to visually display the determined disease name outputted from an output unit into a display window, a sound unit configured to audibly output the determined disease name through the speaker and a transceiver unit configured to transmit and receive the determined disease name to a central medical center or a remote medical office through the antenna.

The telemedical stethoscope of the present invention distinguishes a heart region, a pulmonary region, a neck carotid artery region and a bowel region to set the auscultation mode and auscultation data characteristics are distinguished according to each auscultation mode.

A disease name is determined by auscultating in an order following a heart region auscultation (H mode), a pulmonary region auscultation (P mode), a neck carotid artery region auscultation (N mode) and a bowel region auscultation (B mode) and synthesizing auscultating data when the telemedical stethoscope is primarily used.

That is, a first auscultation is performed on the heart region.

First, when an H mode designation switch is accessed, a display displays a heart figure and a number representing an auscultation region and an auscultation order by an H mode program in a central control unit and a doctor touches a sound collecting plate on a body in that order to listen to a heart sound.

A first auscultation region in the heart region in the display is an aortic artery in a right sternal border at 2nd intercostal space, a second auscultation region is a pulmonic artery in a left sternal border at 2nd intercostal space, a third auscultation region is a tricuspid valve in a right bottom sternal border and a fourth auscultation region is a mitral valve in an apical region.

An auscultation sound around the heart region is a blood flow sound of an aortic artery, a pulmonic artery, a tricuspid valve and a mitral valve.

Therefore, a detected wave is characterized as a peak wave with a constant period.

Also, a detection unit, a filter unit and a database in the central processing unit is operated by an H mode designated program.

The filter unit in the central processing unit passes only peak wave in the heart region according to an H mode designation and removes a wave of the auscultation sound in other body region and a noise wave external of the body to detect an H mode auscultation signal.

Also, an analog peak wave of the passed H mode auscultation signal is converted into a digital signal by an A/D converter, is amplified and is compared with standard data of a designation mode designated in a database (i.e., the H mode). Then the disease name is determined by the central processing unit.

The telemedical stethoscope compares heart region standard data within all standard data in various kinds of diseases to limit search scope and increase diagnosis correctness.

As a comparison result, whether a heart operates is determined as whether there is a heart sound. A disease name is determined as normal pulse, arrhythmia, tachycardia or bradycardia according as a wave period is regular or irregular and a heart rate is slow or fast and is determined as a heart disease based on whether there is a heart murmur.

Also, a second auscultation is performed on the pulmonary region.

When an P mode designation switch is accessed, a display displays a pulmonary figure and a number representing an auscultation region and an auscultation order by an P mode program in a central control unit and a doctor touches a sound collecting plate on a body in that order to listen to a pulmonary sound.

While a patient maintains inhalation, a doctor auscultates an inhalation sound and may perform auscultate twelve times, in more detail six times on a front and six times on a back.

A first auscultation region is a right upper pulmonary region and a second auscultation region is a left upper pulmonary region. A third auscultation region is a right middle pulmonary region and a fourth auscultation region is a left middle pulmonary region. A fifth auscultation region is a right low pulmonary region and a sixth auscultation region is a left low pulmonary region. A pulmonary region in a backside is auscultated in the above region and order.

That is, a wave detected in the pulmonary region is a wave indicating a respiration sound in the lung unlike the heart auscultation.

A disease determination procedure is same with the above heart auscultation case.

The telemedical stethoscope compares P mode standard data in the database with pulmonary region auscultation data to determine pulmonary function according to a respiratory sound per minute. When a wheezing sound occurs in the auscultation region, bronchitis or asthma is generated in the auscultation region and when a crepitant rale occurs in the auscultation region, pneumonia is generated in the auscultation region. When the wheezing sound or crepitant rale is severe, a synthetic medical treatment is expanded.

A third auscultation is performed on the neck carotid artery region auscultation.

When an N mode designation switch is accessed, a display displays a neck figure and a number representing an auscultation region and an auscultation order by an N mode program in a central control unit.

A first auscultation region of a sound collecting plate is a right middle carotid artery region and a second auscultation region is a left middle carotid artery region. A wave detected in the carotid artery region is a wave indicating a blood flow sound.

The telemedical stethoscope compares N mode standard data in the database with neck carotid artery region auscultation data to determine arteriosclerosis in a carotid bruit case and normal blood flow when the neck carotid artery region auscultation data is similar to the N mode standard data.

The telemedical stethoscope determines whether a carotid artery is normal in a neck region.

A fourth auscultation is performed on the bowel region auscultation.

When a B mode designation switch is accessed, a display displays a bowel figure and a number representing an auscultation region and an auscultation order by a B mode program in a central control unit.

A first auscultation region of a sound collecting plate is a right navel region and a second auscultation region is a left navel region. An auscultation sound is a bowel sound (i.e., borborygmus).

The telemedical stethoscope compares B mode standard data in the database with auscultation data to determine bowel movement paralysis when no wave occurs and normal bowel movement when a wave occurs.

In the above, the present invention is described in an auscultation mode, for convenience's sake, according to a normal auscultation order. However, because the present invention obtains auscultation data per auscultation mode, auscultation data in each auscultation mode is same in spite of the auscultation order and a synthetic determination result is same. Therefore, a determination does not influenced when an order of auscultation mode is different.

A disease name is accurately determined based on auscultation data according to four auscultation modes.

Also, the telemedical stethoscope may represent a determination result according to switch operation of a switch block through a display window and a speaker and if necessary, may transmit data by a transceiver unit via antenna to a remote medical center to perform a telemedicine.

Also, the telemedical stethoscope may determine and output a disease name based on auscultation data and couple an attached device linked a health management program storing and managing disease history including an auscultation sound to use for a disease prognosis and personal health management.

Technical Effects

The present invention includes an auscultation mode and mode designation switch in a stethoscope including an audio-visual stethoscope, an automatic determination and storage device and a remote transceiver device to display a figure for an auscultation region and a number for an auscultation order. Therefore, the present invention may compare standard data with detected data by limiting a search scope to the standard data in a designated mode among all standard data in various kinds of diseases and automatically display a disease name and increase diagnosis correctness.

Also, the present invention may store diagnosis data and transmit auscultation data to a doctor in a medical center to receive a telemedicine service. And the present invention may transmit the auscultation data to an attached device linked with a health management program to be helpfully used for a personal health management.

Additional aspects and/or advantages of the invention will be set forth in part in the description which follows and, in part, will be obvious from the description, or may be learned by practice of the invention.

BRIEF DESCRIPTION OF THE DRAWINGS

These and/or other aspects and advantages of the invention will become apparent and more readily appreciated from the following description of the embodiments, taken in conjunction with the accompanying drawings of which.

REFERENCE NUMERAL

1: stethoscope case 1a: sound collecting plate 1b: support plate 2: central control device 3: display window
4: switch block 5: mode switch block 6: speaker 7: antenna

DETAILED DESCRIPTION OF THE EMBODIMENTS

Reference will now be made in detail to the present embodiments of the present invention, examples of which are illustrated in the accompanying drawings, wherein like reference numerals refer to the like elements throughout. The embodiments are described below in order to explain the present invention by referring to the figures.

Figure 1:
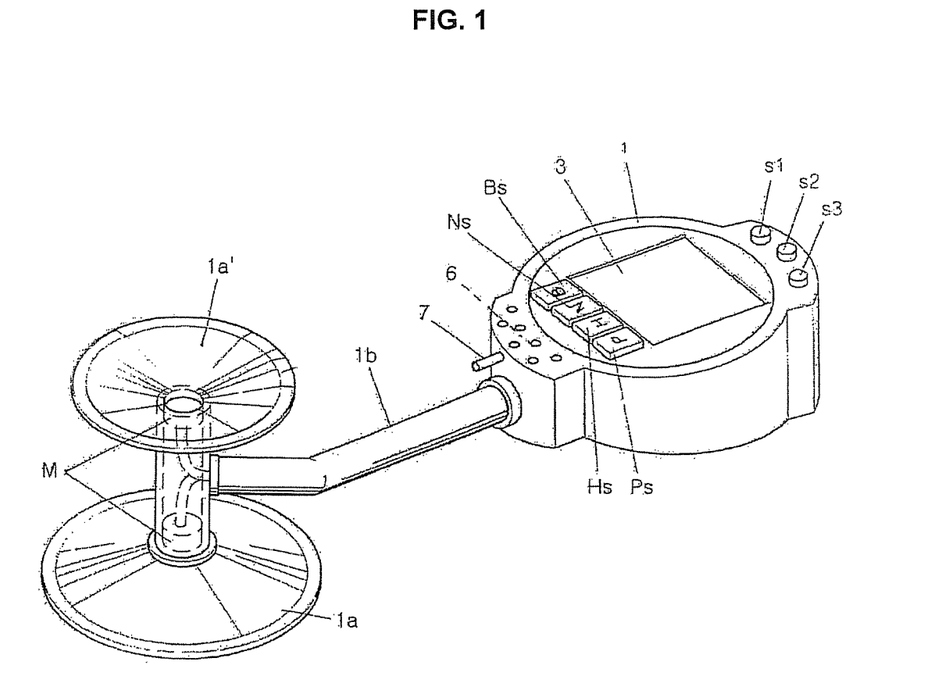
FIG. 1 is a perspective diagram illustrating a stethoscope according to an example embodiment of the present invention.
Figure 2:
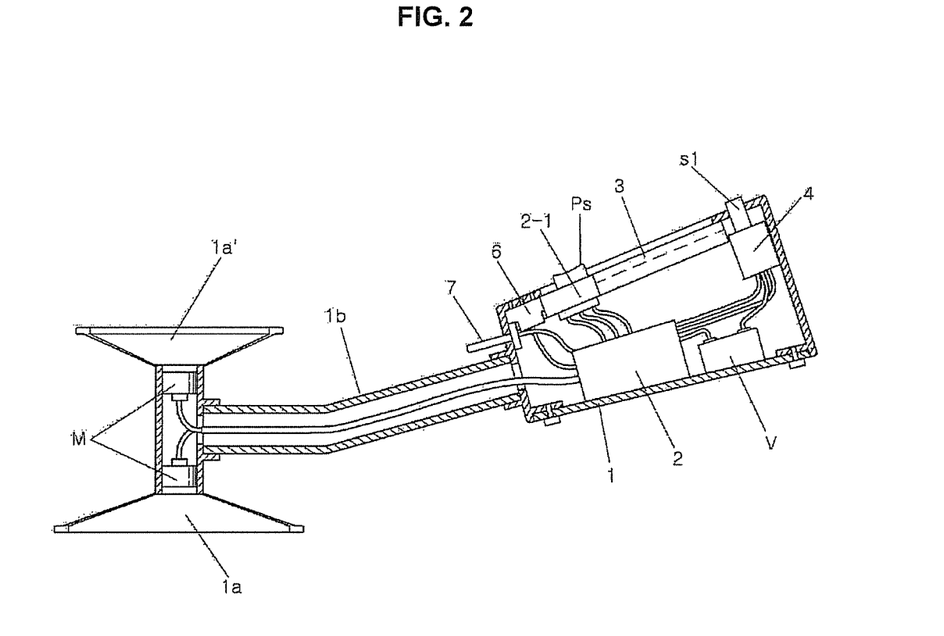
FIG. 2 is a sectional diagram of FIG. 1.

As illustrated in FIGS. 1 and 2, in a telemedical stethoscope, a central control device 2 and a power supply V are built in inner of a case 1 which is integrally equipped with one or more sound collecting plate 1a and 1a' through a support pipe 1b and the one or more sound collecting plate 1a and 1a' embeds an auscultation microphone M. An LCD (Liquid Crystal Display) 3 is built on the case 1, a switch block 4 is built on one side of the case 1 and the switch block 4 includes a power switch s1, a watch switch s2 and a remote transceiver switch s3. A mode switch block 5, a speaker 6 for data auralization and an antenna 7 for remote data transceiver are built on another side of the case 1. The mode switch block 5 includes a designation switch Hs for a heart region auscultation mode, a designation switch Ps for a pulmonary region auscultation mode, a designation switch Ns for a neck carotid artery region auscultation mode and a designation switch Bs for a bowel region auscultation mode.

Figure 3:
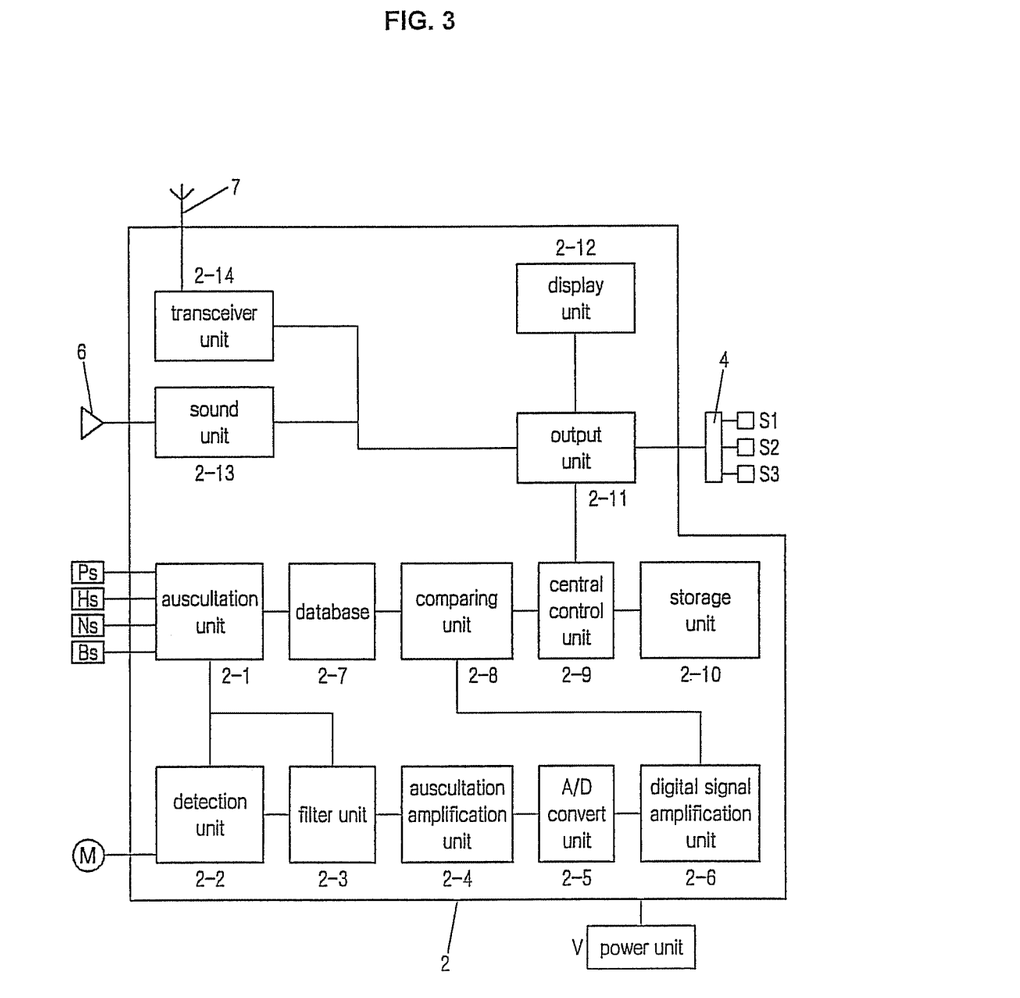
FIG. 3 is a block diagram illustrating a central control device embedded in a stethoscope.

As illustrated in FIG. 3, a central control unit 2-9 in the telemedical stethoscope includes an auscultation unit 2-1 configured to designate an auscultation mode, a detection unit 2-2 for the auscultation microphone M, a filter unit 2-3 configured to filter an auscultation sound of the designated auscultation mode in a detected auscultation sound to remove other auscultation sound in the detected auscultation, an auscultation amplification unit 2-4 configured to amplify the filtered auscultation sound, an ADC unit 2-5 configured to convert an analog signal of the amplified auscultation sound into a digital signal, a digital signal amplification unit 2-6 to amplify the converted digital signal, a database 2-7 storing standard data for various kinds of diseases per the auscultation mode, a comparing unit 2-8 configured to compare the amplified digital signal with the standard data in the auscultation mode, the central control unit 2-9 configured to determine a disease name based on the compared result and to control each unit, a storage unit 2-10 configured to store the determined disease name, a display unit 2-12 configured to visually display the determined disease name outputted from an output unit 2-11 into a display window 3, a sound unit 2-13 configured to audibly output the determined disease name through the speaker 6 and a transceiver unit 2-14 configured to transmit and receive the determined disease name to a central medical center or a remote medical office through the antenna 7.

An auscultation mode in the present invention is set as a heart region (H mode), a pulmonary region (P mode), a neck carotid artery region (N mode) and a bowel region in a digestive system (B mode) and an executing program for each auscultation mode is stored in the central control unit 2-9.

Also, an auscultation order of an auscultation region touching a sound collecting plate in the stethoscope is specified.

Figure 1A:
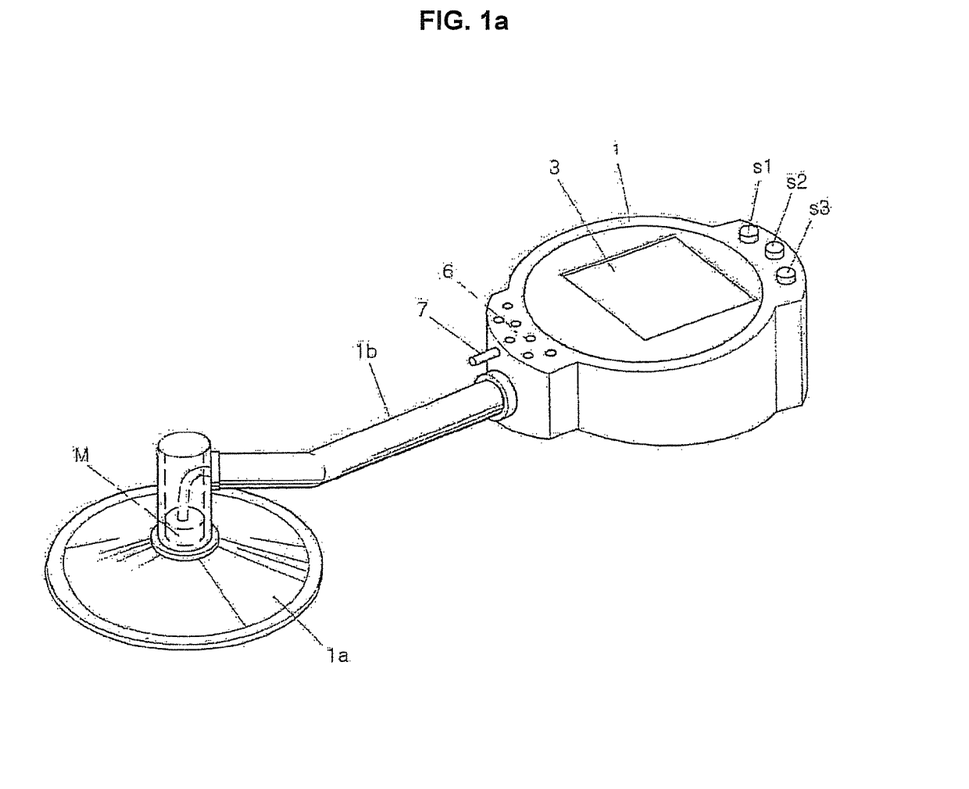
FIG. 1a is a perspective diagram illustrating a stethoscope according to another example embodiment of the present invention.

FIG. 1a is a perspective diagram illustrating a stethoscope having a single sound collecting plate.

The stethoscope of the present invention operates like the following.

When a patient is primarily auscultated, a first auscultation region is a heart region auscultation (H mode), a second auscultation region is a pulmonary region auscultation (P mode), a third auscultation region is a neck region auscultation (N mode) and a fourth auscultation region is a bowel region auscultation (B mode). The auscultation order in the auscultation mode may be situationally changed.

(I) Heart Region Auscultation (H Auscultation Mode)

Figure 4:
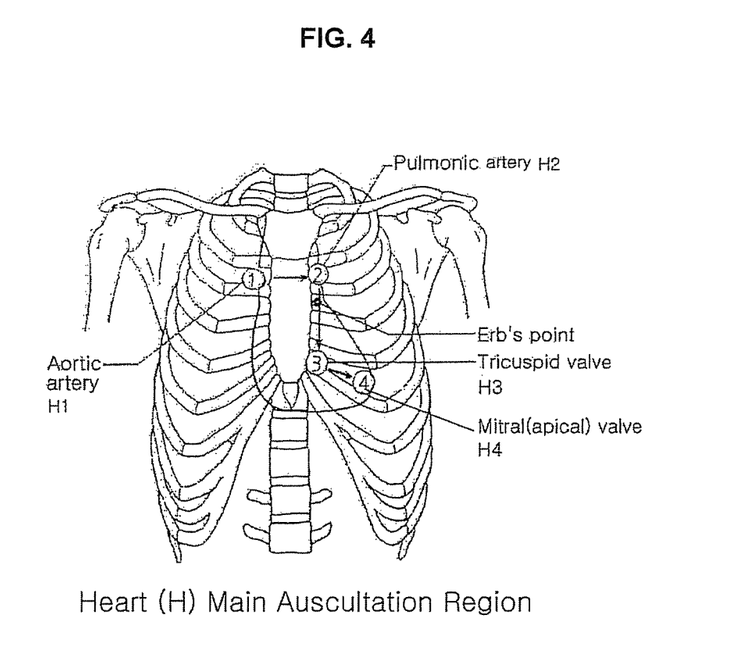
FIG. 4 is an example diagram illustrating a touch area in a sound collecting plate and an auscultation order in a heart region.
Figure 4A:
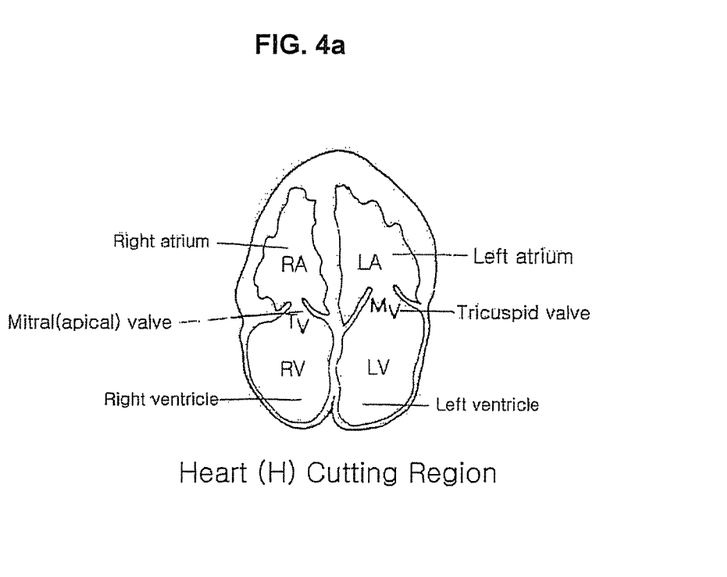
FIG. 4a is a descriptive diagram illustrating a sectional region of a heart.

First, when an H auscultation mode designation switch (Hs) in the stethoscope is accessed, a display 3 displays a heart figure and a number representing an auscultation region and an auscultation order by an H mode program in a central control unit 2-9 in FIG. 4.

A sound collecting plate 1a embedding an auscultation microphone M is touched to a body in a region and an order of ①→②→③→④ in a heart figure in FIG. 4.

Figure 6:
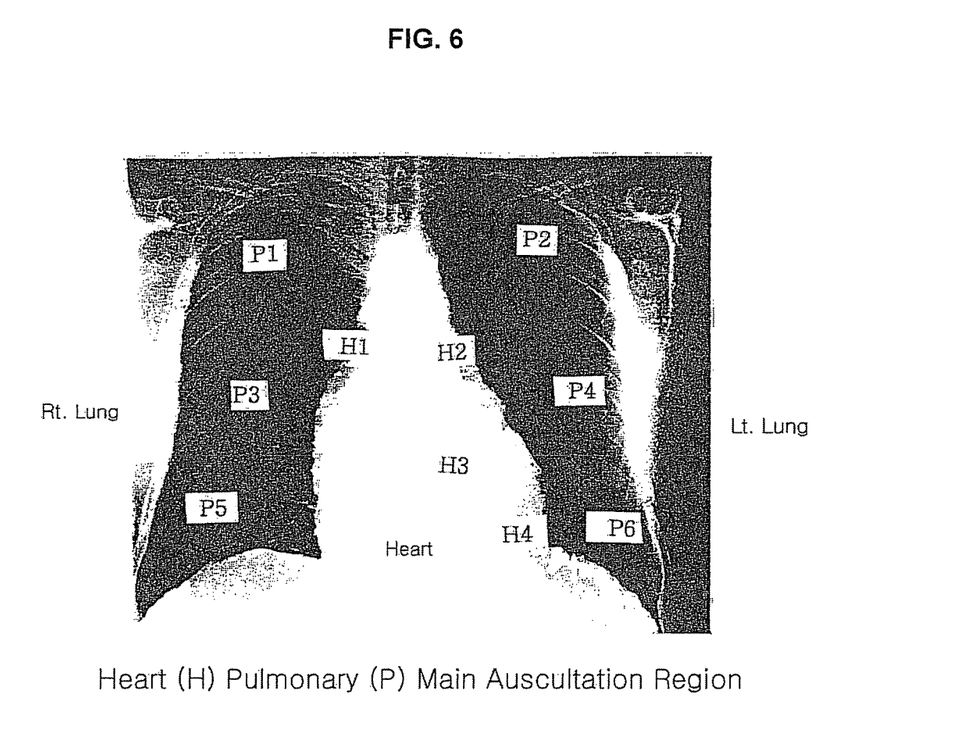
FIG. 6 is an example diagram illustrating a touch area in a sound collecting plate and an auscultation order in a pulmonary region.

As illustrated in FIG. 4 and FIG. 6, the stethoscope auscultates a blood flow sound of main artery in a right parasternal line H1 between the second ribs in a chest, a blood flow sound of a pulmonary artery in a left parasternal line H2 between the second ribs, a blood flow sound of a tricuspid valve in a bottom parasternal line H3 and a blood flow sound of a mitral valve in a apical region H4.

Therefore, a wave of an auscultation sound in a heart region is detected as a peak wave sharp heart sound with a constant period.

Detected auscultation data are inputted to a detection unit 202 of a central control unit 2 so that a noise is removed by the filter unit 2-3. Because the detection unit 2-2 and the filter unit 2-3 is designated as H mode, a peak wave having auscultation data characteristics in the comparison unit 2-8 passes and other noise waves internal and external of a body are filtered through an H mode program.

An H mode auscultation data signal filtered by the filter unit 2-3 is amplified by the auscultation signal amplification unit 3-4, the amplified analog peak wave signal is converted into a digital signal by the A/D converter 2-5 and the converted digital signal is amplified by the digital signal amplification unit 2-6.

The amplified digital data (digital signal) is compared with H mode standard data stored in a database 2-7 in the comparison unit 2-8. Because the database 2-7 is designated as H mode, only standard data designated as an H mode among various kinds of standard auscultation sound data stored in the H mode program are extracted and the extracted standard data is compared with auscultation data detected in the comparison unit 2-8 so that a disease name is determined by the central control unit 2-9. Because only standard data designated as a heart region auscultation mode among various kinds of standard auscultation sound data are compared, a search scope is narrowly limited so that more accurate disease name is determined.

Figure 5:
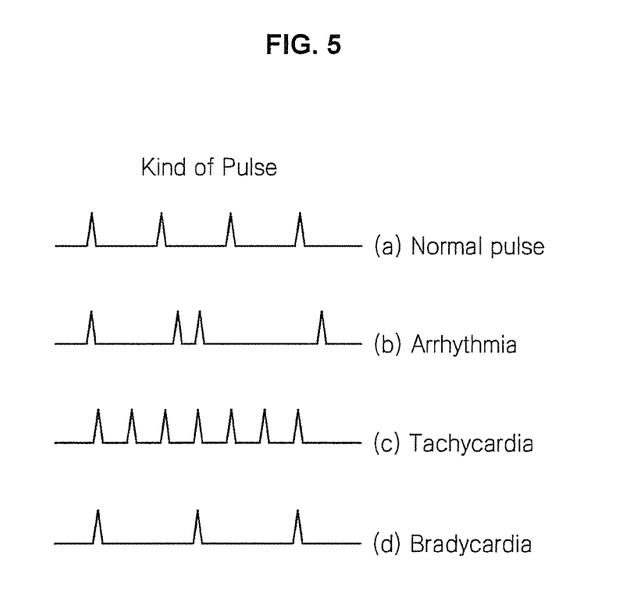
FIG. 5 is an example diagram illustrating an auscultation heart sound in a heart region.

Whether a heart operates is determined based on whether a heart sound exists. As illustrated in FIG. 5(A), when a period of a peak wave is regular, a normal pulse is determined. As illustrated in FIG. 5(B), when a period of a peak wave is irregular, an arrhythmia is determined. As illustrated in FIG. 5(C), when a heart beating per minute is fast, a tachycardia is determined and when a heart beating per minute is slow, a bradycardia is determined. A heart disease name is diagnosed according to a murmur.

Determined information is stored into the storage unit 2-10 and is inputted to the output unit 2-11. The determined information inputted to the output unit 2-11 according to an operation of an audiovisual switch s2 and a transceiver s3 in the switch block 4 is displayed as a character in the display 3 of the stethoscope by the display unit 2-12 and is heard through the speaker 6 by the sound unit 2-13. Also, the determined information is remotely transmitted and received through the antenna 7 by the transmission unit 2-14.

Herein, in a procedure of the detected auscultation data, the contents same with the above heart region auscultation procedure will be omitted.

(II) Pulmonary Region Auscultation (P Auscultation Mode)

When a P mode designation switch (Ps) in the stethoscope is accessed, a display 3 displays a pulmonary figure and a number representing an auscultation region and an auscultation order by a P mode program in a central control unit 2-9 in FIG. 6.

While a patient maintains inhalation, a doctor auscultates an inhalation sound and may perform auscultate twelve times, in more detail, six times on a front and six times on a back.

The sound collecting plate 1a embedding an auscultation microphone M is touched to a body in a region and an order in a pulmonary figure in FIG. 6.

P1 is a right upper pulmonary region and P2 is a left upper pulmonary region. P3 is a right middle pulmonary region and P4 is a left middle pulmonary region. P5 is a right low pulmonary region and P6 is a left low pulmonary region. A pulmonary region in a backside is auscultated in the above region and order.

An auscultation sound wave detected in the pulmonary region is a wave indicating a respiration sound in the lung unlike the heart auscultation sound wave.

Determined auscultation data is processed through a P mode program.

For reading the determined auscultation data, a pulmonary function is determined according to a respiratory degree. When a wheezing sound occurs in the auscultation region, bronchitis or asthma is generated in the auscultation region and when a crepitant rale occurs in the auscultation region, pneumonia is generated in the auscultation region. When the wheezing sound or crepitant rale is severe, a synthetic medical treatment is expanded.

(III) Neck Carotid Artery Region Auscultation Mode (N Auscultation Mode)

Figure 7:
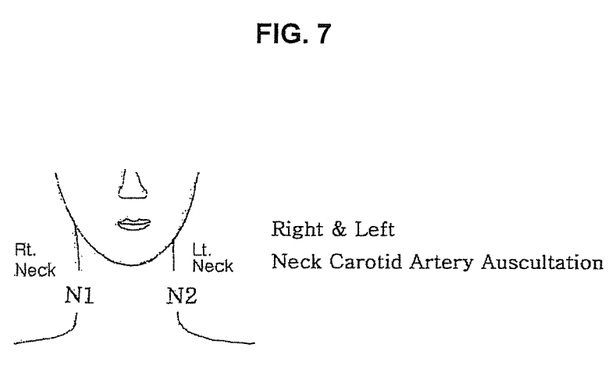
FIG. 7 is an example diagram illustrating a touch area in a sound collecting plate and an auscultation order in a neck region.

When an N mode designation switch (Ns) in the stethoscope is accessed, a display 3 displays a neck figure and a number representing an auscultation region and an auscultation order by an N mode program in a central control unit 2-9 in FIG. 7.

A sound collecting plate 1a embedding an auscultation microphone M is touched to a body in a region and an order of N1→N2 in a neck figure in FIG. 7.

N1 is a right middle carotid artery region in the neck and N2 is a left middle carotid artery region in the neck. A wave detected in the carotid artery region is a wave indicating a blood flow sound.

Auscultation data around the neck is processed through an N mode program.

For reading the determined auscultation data, arteriosclerosis is determined in a carotid bruit case and normal blood flow is determined otherwise.

(IV) Bowel Region Auscultation Mode (B Auscultation Mode)

Figure 8:
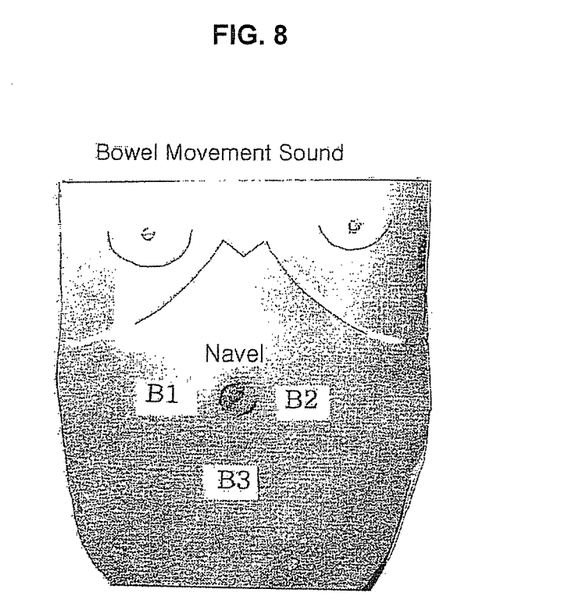
FIG. 8 is an example diagram illustrating a touch area in a sound collecting plate and an auscultation order in a bowel region.

When a B mode designation switch (Bs) in the stethoscope is accessed, a display 3 displays a bowel figure and a number representing an auscultation region and an auscultation order by a B mode program in a central control unit 2-9 in FIG. 8.

A sound collecting plate 1a embedding an auscultation microphone M is touched to a B1, B2, B3 region around a navel in FIG. 8.

B1 is a right navel region and B2 is a left navel region. B3 is a bottom navel region. An auscultation sound is mainly a bowel sound (i.e., borborygmus).

Determined auscultation data is processed through a B mode program.

Bowel movement paralysis is determined when no wave occurs and normal bowel movement is determined when a wave occurs.

As illustrated in the above, the stethoscope may integrate determination of auscultation data respectively obtained according to four auscultation modes to determine a first diagnosis state of a patient. When a more detailed diagnosis is necessary, an integrated electronic diagnostic device is used for more detail investigation.

Also, data determined by the stethoscope according to each switch operation of the switch block may be audiovisually provided and may be remotely transmitted to receive telemedicine service.

Also, a disease name may be determined from detected auscultation data, be stored and be remotely transmitted.

Therefore, a telemedical stethoscope may transmit diagnosis data to an attached device linked a health management program and use for a disease prognosis and personal health management.

A telemedical stethoscope of the present invention may be used in a medical industry area.

In particular, the present invention diagnoses per the auscultation mode and a characteristic of the auscultation data is remarkable. Because only standard data designated as a designated auscultation mode among various kinds of standard auscultation sound data are compared, a search scope is narrowly limited so that more accurate disease name is determined. The auscultated medical information is stored and remotely transmitted to a doctor to be used for a telemedicine service. And the present invention cooperates with an attached device linked with a health management program storing a personal health management record and a disease history such as a pulse sound, a respiratory sound, a bowel movement sound and medical information to be used for a disease prognosis and a personal health management.

Although a few embodiments of the present invention have been shown and described, it would be appreciated by those skilled in the art that changes may be made in this embodiment without departing from the principles and spirit of the invention, the scope of which is defined in the claims and their equivalents.

What is claimed is:

1. A telemedical stethoscope wherein a central control device (2) and a power supply (V) is built in inner of a case (1) which is integrally equipped with a sound collecting plate (1a) through a support pipe (1b), the sound collecting plate (1a) embedding an auscultation microphone (M), wherein an LCD (Liquid Crystal Display) (3) is built on the case (1), wherein a switch block (4) is built on one side of the case (1), the switch block (4) including a power switch (s1), a watch switch (s2) and a remote transceiver switch (s3), and wherein a mode switch block (Hs, Ps, Ns, Bs), a speaker (6) for data auralization and an antenna (7) for remote data transceiver is built on another side of the case (1), the mode switch block (Hs, Ps, Ns, Bs) including a first designation switch (Hs) for a heart region auscultation mode, a second designation switch (Ps) for a pulmonary region auscultation mode, a third designation switch (Ns) for a neck carotid artery region auscultation mode and a fourth designation switch (Bs) for a bowel region auscultation mode.

2. The telemedical stethoscope of claim 1, wherein the central control device (2) in the telemedical stethoscope includes
- an auscultation unit (2-1) configured to designate an auscultation mode,
- a detection unit (2-2) for the auscultation microphone (M),
- a filter unit (2-3) configured to filter an auscultation sound of the designated auscultation mode in a detected auscultation sound to remove other auscultation sound in the detected auscultation,
- an auscultation amplification unit (2-4) configured to amplify the filtered auscultation sound,
- an ADC unit (2-5) configured to convert an analog signal of the amplified auscultation sound into a digital signal,
- a digital signal amplification unit (2-6) to amplify the converted digital signal,
- a database (2-7) storing standard data for various kinds of diseases per the auscultation mode,
- a comparing unit (2-8) configured to compare the amplified digital signal with the standard data in the auscultation mode,
- a central control unit (2-9) configured to determine a disease name based on the compared result and to control each unit,
- a storage unit (2-10) configured to store the determined disease name,
- a display unit (2-12) configured to visually display the determined disease name outputted from an output unit (2-11) into a display window (3),
- a sound unit (2-13) configured to audibly output the determined disease name through the speaker (6) and
- a transceiver unit (2-14) configured to transmit and receive the determined disease name to a central medical center or a remote medical office through the antenna (7).

3. The telemedical stethoscope of claim 1, wherein the telemedical stethoscope auscultates according to an auscultation region and an auscultation order in the auscultation mode designated by the first designation switch (Hs) for the heart region auscultation mode (H), the second designation switch (Ps) for the pulmonary region auscultation mode (P), the third designation switch (Ns) for the neck carotid artery region auscultation mode (N) and the fourth designation switch (Bs) for the bowel region auscultation mode (B), compares auscultation data detected in the auscultation mode with standard data to decode the auscultation data and automatically determine a disease name, and audio-visually stores the auscultation data.

4. The telemedical stethoscope of claim 3, wherein the auscultation mode is classified into the heart region auscultation mode (H), the pulmonary region auscultation mode (P), the neck carotid artery region auscultation mode (N) and the bowel region auscultation mode (B) to be auscultated according to a designation mode.

5. The telemedical stethoscope of claim 1, wherein the telemedical stethoscope transmits diagnosis information for a blood flow sound, a respiratory sound or a gastrointestinal sound to an attached device cooperated with a health management software program of a patient.

6. A telemedical stethoscope comprising:
- a sound collecting plate configured to embed an auscultation microphone (M) therein and to be in contact with a body;
- a designation switch configured to designate an auscultation mode for auscultation though the sound collecting plate (1*a*), the auscultation mode including at least one of a heart region auscultation mode (H), a pulmonary region auscultation mode (P), a neck carotid artery region auscultation mode (N) and a bowel region auscultation mode (B);
- a display unit configured to display an auscultation region and an auscultation order according to the auscultation mode;
- a database configured to store standard data according to the auscultation mode; and
- a central control unit configured to compare auscultation data detected from the body with the standard data to determine a disease name based on the auscultation mode.

7. A telemedical stethoscope comprising:
- a designation switch configured to designate an auscultation mode, the auscultation mode including at least one of a heart region auscultation mode (H), a pulmonary region auscultation mode (P), a neck carotid artery region auscultation mode (N) and a bowel region auscultation mode (B);
- a display unit configured to display an auscultation region and an auscultation order according to the auscultation mode;
- a database configured to store standard data according to the auscultation mode; and
- a central control unit configured to compare auscultation data according to the auscultation mode with the standard data to determine a disease name.

* * * * *